US012611267B2

(12) United States Patent
Blacker

(10) Patent No.: US 12,611,267 B2
(45) Date of Patent: Apr. 28, 2026

(54) DEVICE DRIVE FOR CATHETER PROCEDURE SYSTEM

(71) Applicant: Corindus, Inc., Newton, MA (US)

(72) Inventor: Steven J. Blacker, Framingham, MA (US)

(73) Assignee: Siemens Healthineers Endovascular Robotics, Inc., Newton, MA (US)

( * ) Notice: Subject to any disclaimer, the term of this patent is extended or adjusted under 35 U.S.C. 154(b) by 791 days.

(21) Appl. No.: 18/050,501

(22) Filed: Oct. 28, 2022

(65) Prior Publication Data

US 2023/0112934 A1     Apr. 13, 2023

Related U.S. Application Data

(63) Continuation of application No. 15/175,664, filed on Jun. 7, 2016, now Pat. No. 11,497,565.

(51) Int. Cl.
| | |
|---|---|
| *A61B 34/30* | (2016.01) |
| *A61B 5/00* | (2006.01) |
| *A61B 8/12* | (2006.01) |
| *A61B 34/37* | (2016.01) |
| *A61F 2/95* | (2013.01) |

(Continued)

(52) U.S. Cl.
CPC .............. *A61B 34/30* (2016.02); *A61B 34/37* (2016.02); *A61M 5/142* (2013.01); *A61M 25/0105* (2013.01); *A61B 5/6852* (2013.01); *A61B 8/12* (2013.01); *A61B 2034/301* (2016.02);

(Continued)

(58) Field of Classification Search
CPC ........ A61M 25/09041; A61M 25/0113; A61M 2025/09116; A61M 25/0147; A61B 2034/301; A61B 34/30; A61B 2017/00323; A61B 2034/742; A61B 34/25; A61B 34/35; A61B 34/37; A61B 34/71; A61B 34/74

See application file for complete search history.

(56) References Cited

U.S. PATENT DOCUMENTS

| | | | |
|---|---|---|---|
| 2,970,733 | A | 2/1961 | Soderman |
| 3,821,525 | A | 6/1974 | Eaton et al. |

(Continued)

FOREIGN PATENT DOCUMENTS

| | | |
|---|---|---|
| EP | 1442720 | 8/2004 |
| WO | 2013043872 | 3/2013 |
| WO | 2015189531 | 12/2015 |

OTHER PUBLICATIONS

PCT International Search Report and Written Opinion for PCT/US2017/031917; mail date Aug. 11, 2017; 7 pages.

(Continued)

*Primary Examiner* — Scott J Medway

(57) ABSTRACT

A drive assembly for a catheter procedure includes a body configured to receive a percutaneous device where the body has a first end and a second end. A distal pinch is configured to releasably engage the percutaneous device. A proximal pinch is positioned on the first end of the body and is configured to releasably engage the percutaneous device. A linear drive mechanism is coupled to the body and configured to move the body to cause linear movement of the percutaneous device in a first direction while the proximal pinch is disengaged from the percutaneous device and the distal pinch is engaged with the percutaneous device.

20 Claims, 5 Drawing Sheets

(51) Int. Cl.
| | |
|---|---|
| *A61M 5/00* | (2006.01) |
| *A61M 5/142* | (2006.01) |
| *A61M 25/01* | (2006.01) |
| *A61M 25/10* | (2013.01) |

(52) U.S. Cl.
CPC ............ *A61F 2/9517* (2020.05); *A61M 5/007* (2013.01); *A61M 25/104* (2013.01); *A61M 2205/502* (2013.01)

(56) References Cited

U.S. PATENT DOCUMENTS

| | | | | |
|---|---|---|---|---|
| 5,312,338 | A | 5/1994 | Nelson et al. | |
| 5,350,101 | A | 9/1994 | Godlewski | |
| 5,537,993 | A * | 7/1996 | Reichert | A61M 16/104 |
| | | | | 128/203.14 |
| 6,096,004 | A * | 8/2000 | Meglan | A61B 34/74 |
| | | | | 604/95.01 |
| 6,179,191 | B1 | 1/2001 | Chopp | |
| 6,213,369 | B1 | 4/2001 | Kato | |
| 6,375,471 | B1 | 4/2002 | Wendlandt et al. | |
| 6,669,709 | B1 * | 12/2003 | Cohn | A61B 18/1492 |
| | | | | 606/167 |
| 7,704,223 | B2 * | 4/2010 | Mantell | A61M 13/003 |
| | | | | 604/24 |
| 7,717,865 | B2 | 5/2010 | Boutillette et al. | |
| 7,766,894 | B2 | 8/2010 | Weitzner et al. | |
| 8,403,860 | B2 | 3/2013 | Patangay et al. | |
| 8,584,701 | B2 * | 11/2013 | Duncan | A61M 39/223 |
| | | | | 116/277 |
| 8,840,627 | B2 | 9/2014 | Mathelin et al. | |
| 9,017,281 | B2 * | 4/2015 | Mastri | A61B 17/3417 |
| | | | | 604/26 |
| 9,095,681 | B2 | 8/2015 | Wenderow et al. | |
| 9,375,539 | B2 * | 6/2016 | Stearns | B01D 46/4254 |
| 9,452,018 | B2 | 9/2016 | Yu | |
| 10,653,863 | B1 * | 5/2020 | Blacker | A61M 25/0158 |
| 12,433,702 | B2 * | 10/2025 | Hutter | A61B 34/30 |
| 2003/0097884 | A1 | 5/2003 | Sund et al. | |
| 2004/0112436 | A1 | 6/2004 | Dille | |
| 2004/0153027 | A1 * | 8/2004 | Mantell | A61M 16/202 |
| | | | | 604/23 |
| 2007/0078385 | A1 | 4/2007 | Accisano et al. | |
| 2009/0082722 | A1 | 3/2009 | Munger et al. | |
| 2011/0282150 | A1 | 11/2011 | Yamakawa et al. | |
| 2011/0290854 | A1 | 12/2011 | Timm et al. | |
| 2014/0276389 | A1 | 9/2014 | Walker | |
| 2015/0105650 | A1 | 4/2015 | Burkett | |
| 2015/0142013 | A1 | 5/2015 | Tanner et al. | |
| 2015/0148816 | A1 | 5/2015 | Govari et al. | |
| 2017/0156802 | A1 | 6/2017 | Deboeuf et al. | |
| 2017/0348060 | A1 | 12/2017 | Blacker | |
| 2020/0282186 | A1 * | 9/2020 | Blacker | A61M 25/09041 |
| 2024/0000524 | A1 * | 1/2024 | Gregory | A61B 34/30 |

OTHER PUBLICATIONS

Translation of Publication WO 2015189531; Fournier, et al.; published on Dec. 17, 2015 and translated Jun. 1, 2016; 49 pages.

* cited by examiner

DEVICE DRIVE FOR CATHETER PROCEDURE SYSTEM

CROSS-REFERENCE TO RELATED APPLICATIONS

This is a continuation application of U.S. application Ser. No. 15/175,664, filed Jun. 7, 2016, the contents of which are incorporated by reference herein for all purposes.

FIELD OF THE INVENTION

The present invention relates generally to the field of catheter systems for performing therapeutic procedures and in particular, to a device drive for a catheter procedure system.

BACKGROUND OF THE INVENTION

Catheters may be used for many medical procedures, including inserting a guide wire, delivering a stent and delivering and inflating a balloon. Catheterization procedures are commonly performed for diagnosis and treatment of diseases of the heart and vascular systems. The catheterization procedure is generally initiated by inserting a guide wire into a blood vessel in the patient's body. The guide wire is then advanced to the desired location, most commonly in one of the heart vessels or elsewhere in the vascular system. At this point, a catheter is slid over the guide wire into the blood vessel and/or heart. In some procedures, the catheter is a balloon catheter or stent delivery system that when deployed at the site of the lesion allows for increased blood flow through the portion of the coronary artery that is affected by the lesion.

For manual insertion of a guide wire, the physician applies torque and axial push force on the proximal end of a guide wire to effect tip direction and axial advancement at the distal end. Robotic catheter procedure systems have been developed that may be used to aid a physician in performing a catheterization procedure such as a percutaneous coronary intervention (PCI). The physician uses a robotic system to precisely steer a coronary guide wire, balloon catheter or stent delivery system in order to, for example, widen an obstructed artery. In order to perform PCI, the distal tip of a guide wire must be navigated through coronary anatomy past a target lesion. While observing the coronary anatomy using fluoroscopy, the physician manipulates the proximal end of the guide wire in order to direct the distal tip into the appropriate vessels toward the lesion and avoid advancing into side branches. A robotic catheter procedure system includes drive mechanisms to drive various elongated medical devices (e.g., guide wire, guide catheter, working catheter) used in catheterization procedures to provide linear and rotational movement of the elongated medical device.

It would be desirable to provide a device drive for a catheter procedure system that is responsive to user input to manipulate an elongated medical device where the linear and rotary movements are independent.

SUMMARY OF THE INVENTION

In accordance with an embodiment, a drive assembly for a catheter procedure system includes a body configured to receive a percutaneous device, the body having a first end and a second end, a distal pinch configured to releasably engage the percutaneous device, a proximal pinch positioned on the first end of the body, the proximal pinch configured to releasably engage the percutaneous device, a linear drive mechanism coupled to the body, the linear drive mechanism configured to move the body to cause linear movement of the percutaneous device in a second direction opposite the first direction while the proximal pinch is disengaged from the percutaneous device and the distal pinch is engaged with the percutaneous device.

In accordance with another embodiment, a catheter procedure system includes a bedside system including at least one drive assembly, the drive assembly including a body configured to receive a percutaneous device, the body having a first end and a second end, a distal pinch configured to releasably engage the percutaneous device, a proximal pinch positioned on the first end of the body, the proximal pinch configured to releasably engage the percutaneous device, a linear drive mechanism coupled to the body, the linear drive mechanism configured to move the body to cause linear movement of the percutaneous device in a first direction while the proximal pinch is disengaged from the percutaneous device and the distal pinch is engaged with the percutaneous device.

BRIEF DESCRIPTION OF THE DRAWINGS

This application will become more fully understood from the following detailed description, taken in conjunction with the accompanying figures, wherein like reference numerals refer to like elements in which.

DETAILED DESCRIPTION OF THE PREFERRED EMBODIMENTS

Figure 1:
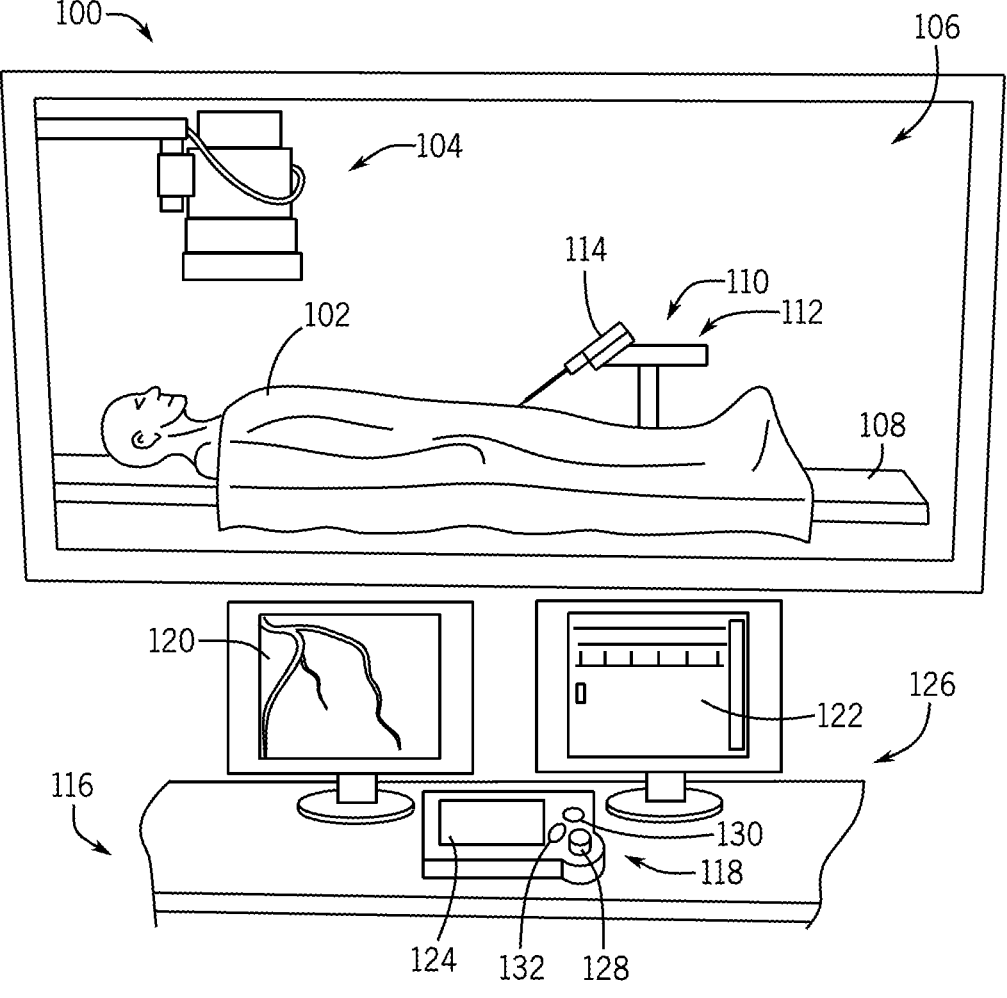
FIG. 1 is a perspective view of an exemplary catheter procedure system in accordance with an embodiment.

FIG. 1 is a perspective view of an exemplary catheter procedure system in accordance with an embodiment. In FIG. 1, a catheter procedure system 100 may be used to perform catheter based medical procedures (e.g., a percutaneous intervention procedure). Catheter based medical procedures may include diagnostic catheterization procedures during which one or more catheters are used to aid in the diagnosis of a patient's disease. For example, during one embodiment of a catheter based diagnostic procedure, a contrast media is injected onto one or more coronary arteries through a catheter and an image of the patient's heart is taken. Catheter based medical procedures may also include catheter based therapeutic procedures (e.g., angioplasty, stent placement, treatment of peripheral vascular disease, etc.) during which a catheter is used to treat a disease. It should be noted, however, that one skilled in the art would recognize that certain specific percutaneous intervention devices or components (e.g., type of guide wire, type of catheter, etc.) will be selected based on the type of procedure that is to be performed. Catheter procedure system 100 is capable of performing any number of catheter based medical procedures with minor adjustments to accommodate the specific percutaneous intervention devices to be used in the procedure. In particular, while the embodiments of catheter procedure system 100 describe herein are explained primarily in relation to the treatment of coronary disease, catheter procedure system 100 may be used to diagnose and/or treat any type of disease or condition amenable to diagnosis and/or treatment via a catheter based procedure.

Catheter procedure system 100 includes lab unit 106 and workstation 116. Catheter procedure system 100 includes a robotic catheter system, shown as bedside system 110, located within lab unit 106 adjacent a patient 102. Patient 102 is supported on a table 108. Generally, bedside system 110 may be equipped with the appropriate percutaneous intervention devices or other components (e.g., guide wires, guide catheters, working catheters such as balloon catheters and stent delivery systems, contrast media, medicine, diagnostic catheters, etc.) to allow the user to perform a catheter based medical procedure via a robotic system by operating various controls such as the controls located at workstation 116. Bedside system 110 may include any number and/or combination of components to provide bedside system 110 with the functionality described herein. Bedside system 110 includes, among other elements, a drive assembly 114 (e.g., that may contain a sterile, disposable portion) supported by a robotic arm 112 which may be used to automatically advance a guide wire into a guide catheter seated in an artery of the patient 102.

Bedside system 110 is in communication with workstation 116, allowing signals generated by the user inputs of workstation 116 to be transmitted to bedside system 110 to control the various functions of bedside system 110. Bedside system 110 may also provide feedback signals (e.g., operating conditions, warning signals, error codes, etc.) to workstation 116. Bedside system 110 may be connected to workstation 116 via a communication link 140 (shown in FIG. 2) that may be a wireless connection, cable connections, or any other means capable of allowing communication to occur between workstation 116 and bedside system 110.

Workstation 116 includes a user interface 126 configured to receive user inputs to operate various components or systems of catheter procedure system 100. User interface 126 includes controls 118 that allow the user to control bedside system 110 to perform a catheter based medical procedure. For example, controls 118 may be configured to cause bedside system 110 to perform various tasks using the various percutaneous intervention devices with which bedside system 110 may be equipped (e.g., to advance, retract, or rotate a guide wire, advance, retract or rotate a working catheter, advance, retract, or rotate a guide catheter, inflate or deflate a balloon located on a catheter, position and/or deploy a stent, inject contrast media into a catheter, inject medicine into a catheter, or to perform any other function that may be performed as part of a catheter based medical procedure). Drive assembly 114 includes various drive mechanisms to cause movement (e.g., axial and rotational movement) of the components of the bedside system 110 including the percutaneous devices.

In one embodiment, controls 118 include a touch screen 124, one or more joysticks 128 and buttons 130, 132. The joystick 128 may be configured to advance, retract, or rotate various components and percutaneous devices such as, for example, a guide wire, a guide catheter or a working catheter. Buttons 130, 132 may include, for example, an emergency stop button and a multiplier button. When an emergency stop button is pushed a relay is triggered to cut the power supply to bedside system 110. Multiplier button acts to increase or decrease the speed at which the associated component is moved in response to a manipulation of controls 118. In one embodiment, controls 118 may include one or more controls or icons (not shown) displayed on touch screen 124, that, when activated, causes operation of a component of the catheter procedure system 100. Controls 118 may also include a balloon or stent control that is configured to inflate or deflate a balloon and/or a stent. Each of the controls may include one or more buttons, joysticks, touch screen, etc. that may be desirable to control the particular component to which the control is dedicated. In addition, touch screen 124 may display one or more icons (not shown) related to various portions of controls 118 or to various components of catheter procedure system 100.

User interface 126 may include a first monitor or display 120 and a second monitor or display 122. First monitor 120 and second monitor 122 may be configured to display information or patient specific data to the user located at workstation 116. For example, first monitor 120 and second monitor 122 may be configured to display image data (e.g., x-ray images, MRI images, CT images, ultrasound images, etc.), hemodynamic data (e.g., blood pressure, heart rate, etc.), patient record information (e.g., medical history, age, weight, etc.). In addition, first monitor 120 and second monitor 122 may be configured to display procedure specific information (e.g., duration of procedure, catheter or guide wire position, volume of medicine or contrast agent delivered, etc.). Monitor 120 and monitor 122 may be configured to display information regarding the position the guide catheter. Further, monitor 120 and monitor 122 may be configured to display information to provide the functionalities associated with controller 134 (shown in FIG. 2) discussed below. In another embodiment, user interface 126 includes a single screen of sufficient size to display one or more of the display components and/or touch screen components discussed herein.

Catheter procedure system 100 also includes an imaging system 104 located within lab unit 106. Imaging system 104 may be any medical imaging system that may be used in conjunction with a catheter based medical procedure (e.g., non-digital x-ray, digital x-ray, CT, MRI, ultrasound, etc.). In an exemplary embodiment, imaging system 104 is a digital x-ray imaging device that is in communication with workstation 116. In one embodiment, imaging system 104 may include a C-arm (not shown) that allows imaging system 104 to partially or completely rotate around patient 102 in order to obtain images at different angular positions relative to patient 102 (e.g., sagittal views, caudal views, anterior-posterior views, etc.).

Imaging system 104 may be configured to take x-ray images of the appropriate area of patient 102 during a particular procedure. For example, imaging system 104 may be configured to take one or more x-ray images of the heart to diagnose a heart condition. Imaging system 104 may also be configured to take one or more x-ray images during a catheter based medical procedure (e.g., real time images) to assist the user of workstation 116 to properly position a guide wire, guide catheter, stent, etc. during the procedure. The image or images may be displayed on first monitor 120 and/or second monitor 122. In particular, images may be displayed on first monitor 120 and/or second monitor 122 to allow the user to, for example, accurately move a guide catheter into the proper position.

In addition, a user of workstation 116 may be able to control the angular position of imaging system 104 relative to the patient to obtain and display various views of the patient's heart on first monitor 120 and/or second monitor 122. Displaying different views at different portions of the procedure may aid the user of workstation 116 to properly move and position the percutaneous interventional devices within the 3D geometry of the patient's heart. In an embodiment, imaging system 104 may be a 2D imaging system. In another embodiment, imaging system 104 may be any 3D imaging modality such as an x-ray based computed tomography (CT) imaging device, a magnetic resonance imaging device, a 3D ultrasound imaging device, etc. In this embodiment, the image of the patient's heart that is displayed during the procedure may be a 3D image. In addition, controls 118 may also be configured to allow the user positioned at workstation 116 to control various functions of imaging system 104 (e.g., image capture, magnification, collimation, c-arm positioning, etc.).

Figure 2:
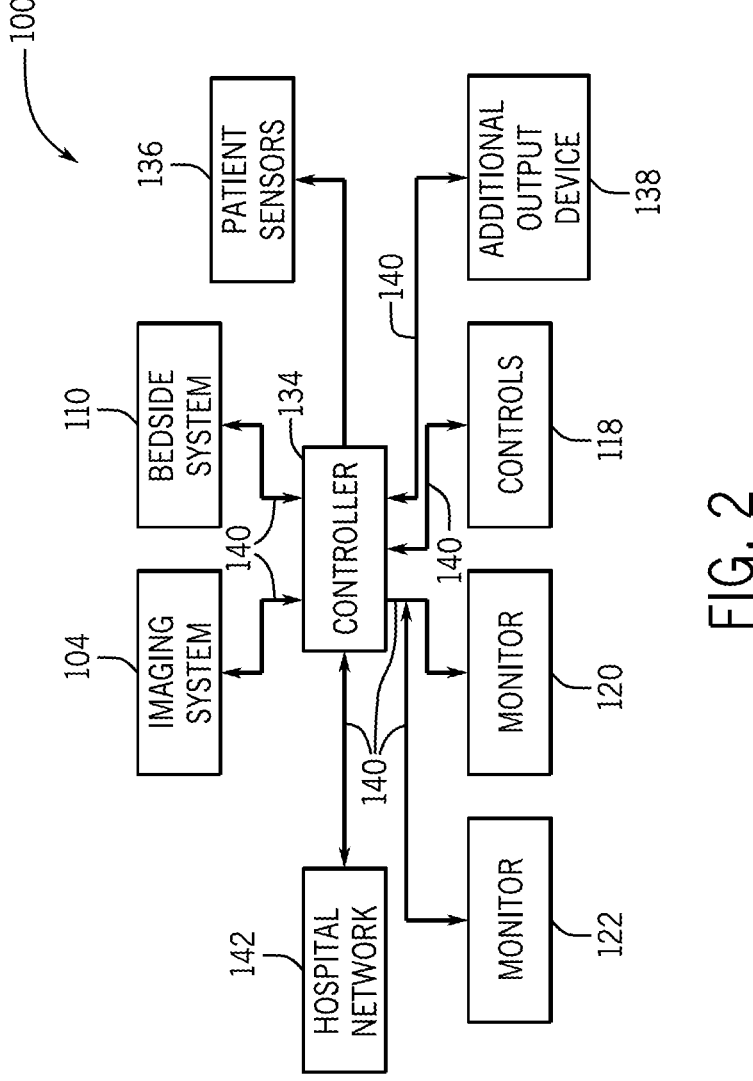
FIG. 2 is a schematic block diagram of a catheter procedure system in accordance with an embodiment.

Referring to FIG. 2, a block diagram of catheter procedure system 100 is shown according to an exemplary embodiment. Catheter procedure system 100 may include a control system, shown as controller 134. Controller 134 may be part of workstation 116. Controller 134 may generally be an electronic control unit suitable to provide catheter procedure system 100 with the various functionalities described herein. For example, controller 134 may be an embedded system, a dedicated circuit, a general purpose system programmed with the functionality described herein, etc. Controller 134 is in communication with one or more bedside systems 110, controls 118, monitors 120 and 122, imaging system 104 and patient sensors 136 (e.g., electrocardiogram ("ECG") devices, electroencephalogram ("EEG") devices, blood pressure monitors, temperature monitors, heart rate monitors, respiratory monitors, etc.). In various embodiments, controller 134 is configured to generate control signals based on the user's interaction with controls 118 and/or based upon information accessible to controller 134 such that a medical procedure may be performed using catheter procedure system 100. In addition, controller 134 may be in communication with a hospital data management system or hospital network 142 and one or more additional output devices 138 (e.g., printer, disk drive, cd/dvd writer, etc.).

Communication between the various components of catheter procedure system 100 may be accomplished via communication links 140. Communication links 140 may be dedicated wires or wireless connections. Communication links 140 may also represent communication over a network. Catheter procedure system 100 may be connected or configured to include any other systems and/or devices not explicitly shown. For example, catheter procedure system 100 may include IVUS systems, image processing engines, data storage and archive systems, automatic balloon and/or stent inflation systems, medicine injection systems, medicine tracking and/or logging systems, user logs, encryption systems, systems to restrict access or use of catheter procedure system 100, etc.

Figure 3:
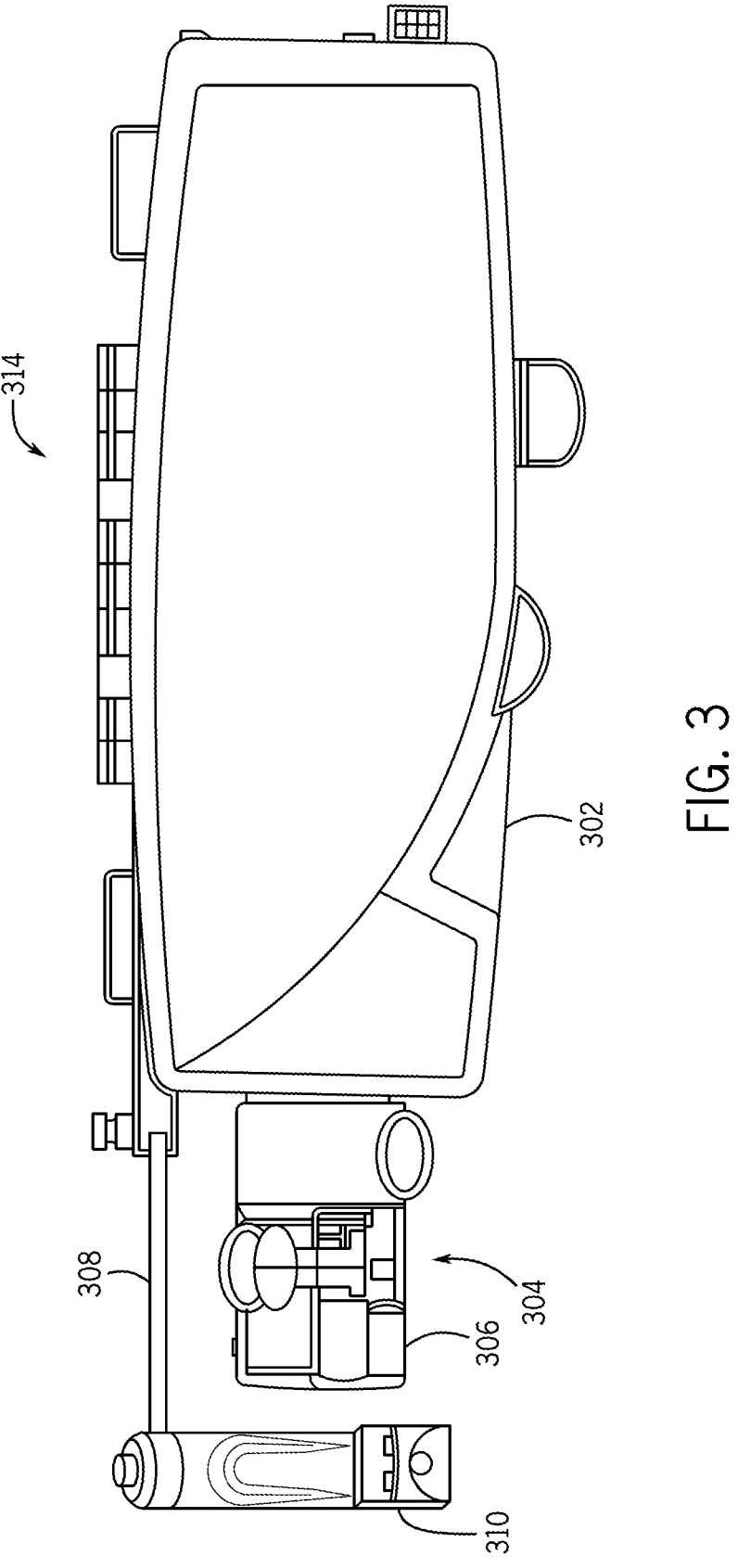
FIG. 3 is a top view of an exemplary drive assembly housing in accordance with an embodiment.

As mentioned, bedside system 110 (shown in FIG. 1) includes a drive assembly 114 which may be used to automatically advance various percutaneous devices (e.g., a guide wire, a guide catheter, a working catheter, etc.). FIG. 3 is a top view of an exemplary drive assembly housing in accordance with an embodiment. In FIG. 3, the drive assembly housing is shown as a cassette 314. Cassette 314 includes a housing 302 and may be mounted on a base (not shown). Cassette 314 may be equipped with percutaneous devices (not shown) to allow a user to perform a catheterization procedure. Cassette 314 includes a y-connector support assembly 304 used to releasably house a y-connector (not shown). Y-connector support assembly 304 includes a chassis 306. Cassette 314 also includes a guide catheter support 310 that supports a guide catheter (not shown) at a position spaced apart from the cassette 314. The guide catheter support 310 is attached to the cassette 314 by a rod 308. In one embodiment, rod 310 is telescoping so that the guide catheter support 310 may be moved away from the cassette 314. The guide catheter support 310 supports a guide catheter at a position spaced apart from the cassette 314, between the patient and the cassette 314, to prevent buckling, bending, etc. of the portion of the guide catheter between the cassette 314 and the patient.

Figure 4:
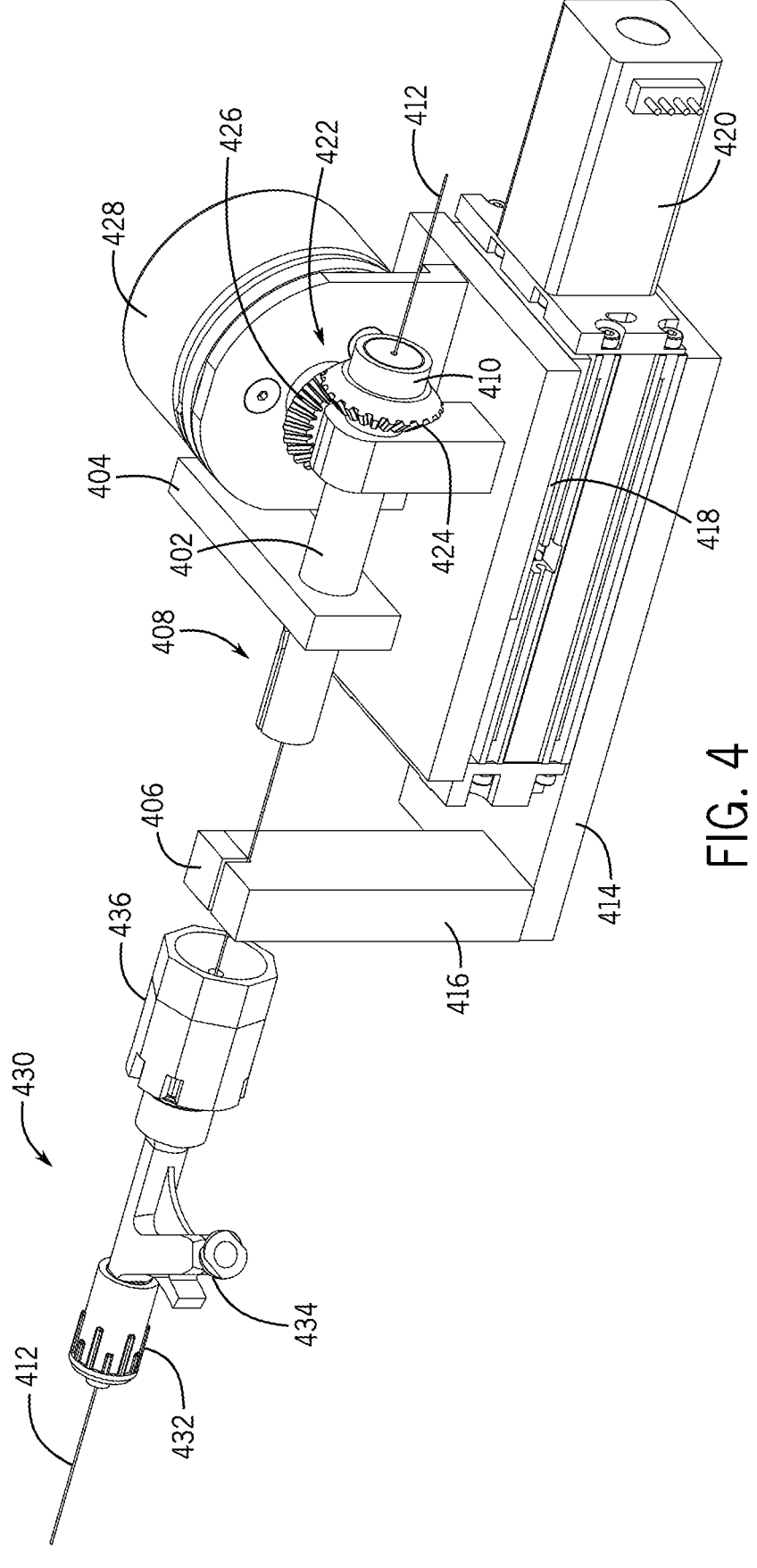
FIG. 4 is a perspective view of a drive assembly in accordance with an embodiment.
Figure 5:
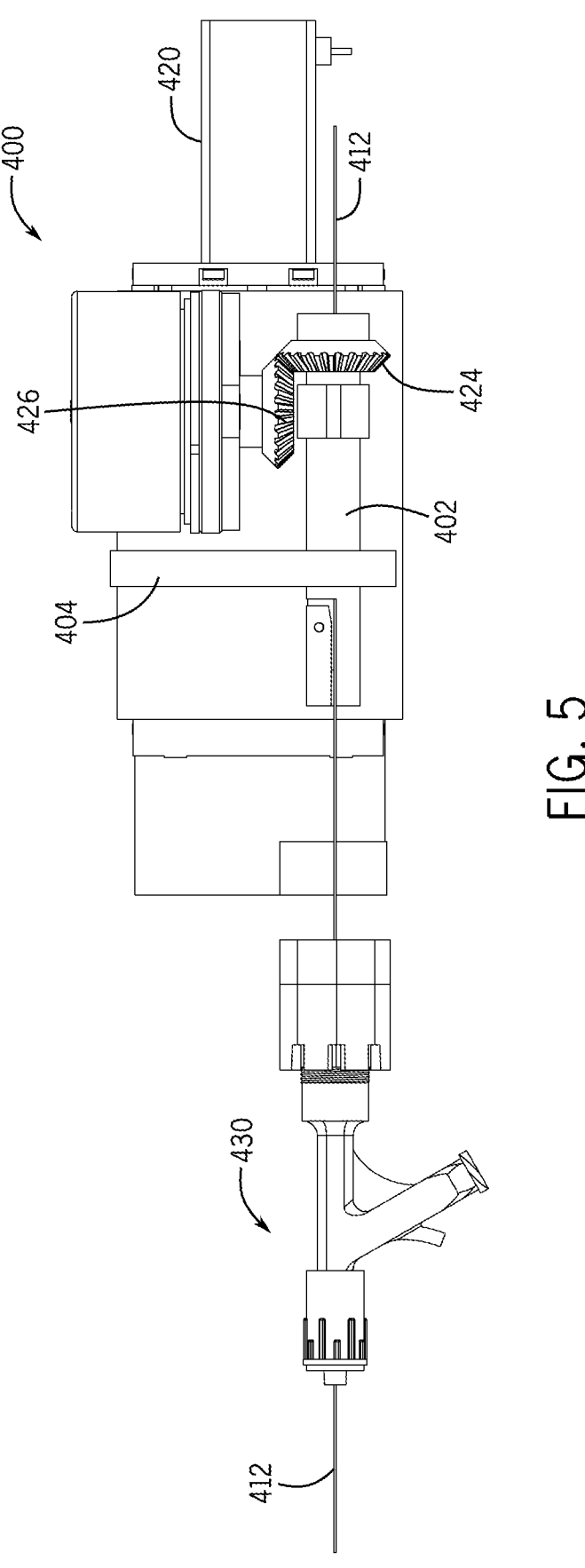
FIG. 5 is a top view of a drive assembly in accordance with an embodiment.

Cassette 314 is also configured to house various drive mechanisms to cause movement (e.g., axial and rotational movement) of the components of the bedside system including the percutaneous devices. FIG. 4. is a perspective view of a drive assembly in accordance with an embodiment and FIG. 5 is a top view of a drive assembly in accordance with an embodiment. Drive assembly 400 may be disposed within a housing such as cassette 314 (shown in FIG. 3). The housing may be designed to provide a sterile interface for elements that engage the percutaneous devices. In various embodiments, one or more elements of the drive assembly (discussed below) may be disposed within a housing. Various elements of the drive assembly 400 may be removable from the housing. Drive assembly 400 is configured to drive, for example, to advance, to retract and to rotate, percutaneous devices, such as a guide wire 412, used in a catheter procedure system. While a guide wire 412 is shown in FIGS. 4 and 5, it should be understood that drive assembly 400 may be used to drive other percutaneous devices such as a , a guide catheter, a working catheter (e.g., a balloon catheter, a stent delivery system), fractional flow reserve (FFR) devices, intervascular ultrasound (IVUS) devices or other elongated medical devices. In one embodiment, one drive assembly may be used to drive the various percutaneous devices used in the catheter procedure system. In another embodiment more than one drive assembly 400 may be used, for example, one drive assembly for a guide wire and one drive assembly for a working catheter. In other embodiment, the various elements of the drive assembly 400 may be customized for a particular percutaneous device, for example, for different size wires or catheters.

Drive assembly 400 includes a body 402, a proximal pinch or grip 404 and a distal pinch or grip 406. Body 402 has a first end 408 and a second end 410. The guide wire 412 is positioned within the body 402. In one embodiment, the body 402 may be side loadable to allow for placement of the percutaneous interventional device in the body 402. Proximal pinch 404 is positioned on the first end 408 of body 402. Proximal pinch 404 is configured to releasably engage percutaneous interventional deice such as, for example, a guide wire 412. Proximal pinch may be any mechanism configured to alternately engage with and disengage from the guide wire 412, for example, a bi-stable mechanism or collet. Proximal pinch 404 may be actuated pneumatically, hydraulically, electrically or by other known methods. In one embodiment, proximal pinch 404 is configured to quickly release from the percutaneous device.

Distal pinch 406 is positioned on a vertical support 416 connected to a base 414 of drive assembly 400. Distal pinch 406 is configured to releasably engage a percutaneous interventional device such as, for example, the guide wire 412. Distal pinch 406 may be any mechanism configured to alternately engage with and disengage from the guide wire 412, for example, a bi-stable mechanism or collet. Distal pinch 406 may be actuated pneumatically, hydraulically, electrically, or by other known methods. In one embodiment, distal pinch 406 is configured to quickly release from the percutaneous device. Distal pinch 406 is spaced apart from the proximal pinch 404 when proximal pinch 404 is in a first position shown in FIG. 4 and discussed further below.

Drive assembly 400 includes a linear drive mechanism 418, shown in FIGS. 4 and 5 as a linear slide. Linear drive mechanism 418 may be other types of mechanisms that can be used to generate linear motion or substantially linear motion such as, for example, a four bar linkage. A linear motor 420 is coupled to the linear drive mechanism 418. In one embodiment, linear motor 420 is disposed within the housing 302 (shown in FIG. 3) of the cassette. In other embodiments, linear motor 420 may be located outside of the cassette and connected to linear drive mechanism 418 via an appropriate transmission device (e.g., shaft, cable, other mechanical coupler, etc.). Linear drive mechanism 418 and linear motor 420 are configured to cause linear movement of the guide wire 412 (e.g., advance and retract) along the longitudinal axis of the guide wire 412. Drive assembly 400 also includes a rotational drive mechanism 422, shown in FIGS. 4 and 5 as a first gear 424 positioned on the second end 410 of the body 402 and a second gear 426 coupled to a rotary motor 428. First gear 424 and second gear 426 are in mechanical contact. In one embodiment, rotary motor 428 is disposed within the housing 302 (shown in FIG. 3) of the cassette. In other embodiments, rotary motor 428 may be located outside of the cassette and connected to rotational drive mechanism 422 via an appropriate transmission device (e.g., shaft, cable, other mechanical coupler, etc.). Rotational drive mechanism 422 and rotary motor 428 are configured to cause rotation of the body 402 and proximal pinch 404 to cause the guide wire 412 to rotate about its longitudinal axis. In another embodiment, if the percutaneous device being driven does not require rotation, drive assembly 400 may not include a rotational drive mechanism 422.

In FIGS. 4 and 5, a y-connector 430 is shown that may be coupled to the cassette via, for example, a y-connector support assembly 304 (shown in FIG. 3). Y-connector 430 includes a first leg 432, a second leg 434 and a third leg 436. First leg 432 is configured to attach to a guide catheter (not shown) such that the central lumen of the y-connector is in fluid communication with the central lumen of the guide catheter. Second leg 434 is angled away from the longitudinal axis of y-connector 430. Second leg 434 of y-connector 430 allows introduction of a contrast agent or medicine into the lumen of the guide catheter. Third leg 436 extends away from the guide catheter toward drive assembly 400. In use, the percutaneous device (e.g., guide wire 412) is inserted into the third leg 436 of y-connector 430 and may be advanced through y-connector 430 into the lumen of the guide catheter. The third leg 436 also includes a one-way valve that permits insertion and removal of the percutaneous device but prohibits bodily fluid from exiting third leg 436. In one embodiment, third leg 436 may be configured to act as the distal pinch 406. For example, third leg 436 may include a valve that is configured to pinch the device or to provide adequate friction to maintain the device's position (e.g., a sealing clamp).

In operation, drive assembly 400 may be used to generate linear movement and rotational movement of the guide wire 412. In one embodiment, advancement or retraction of the guide wire 412 is done independently of the rotation of the guide wire 412. In other embodiment, the guide wire 412 may be rotated as it is being advanced or retracted. For advancement of the guide wire 412, the proximal pinch 404 is actuated to engage (e.g. grip or pinch) the guide wire 412. In FIGS. 4 and 5, proximal pinch 404 is shown as a bar that may be advanced along first end 408 of body 402 to engage guide wire 412. The distal pinch 406 is then actuated to disengage from the guide wire 412. Preferably, the engagement and disengagement of the proximal pinch 404 is independent of the orientation of the body 402. Distal pinch 408 is engaged only when proximal pinch 404 is disengaged. Accordingly, distal pinch 406 may be used to hold and support guide wire 412 when proximal pinch 404 is disengaged and readjusts its position. Linear drive mechanism 418 is then used to advance body 402, proximal pinch 404 and guide wire 412 a predetermined distance from a first position to a second position that is proximate to the distal pinch 406. Preferably, the distance the guide wire 412 or other percutaneous device is moved by linear drive mechanism 418 (e.g., the stroke length) is based on the axial stiffness of the percutaneous device. In addition, the stroke length may also be based on how coaxial the percutaneous device is with the device into which it is being advanced (e.g., an introducer sheath or guide catheter). Accordingly, a stroke length may be selected that is appropriate for the particular percutaneous device. After the guide wire 412 is advanced to the second position, the distal pinch 406 is actuated to engage (e.g., grip or pinch) to fix the guide wire 412. Proximal pinch 404 is then actuated to disengage from or release the guide wire 412. Linear drive mechanism 418 is then used to retract the body 402 and proximal pinch 404 and return to the first position. Once proximal pinch 404 is returned to the first position, the process may begin again to advance the guide wire 412 by another stroke length. Accordingly, proximal pinch 404 is actuated to engage the guide wire 412. Distal pinch 406 is then disengaged and guide wire 412 may be advanced the stroke length distance. The steps to advance the guide wire 412 with drive assembly 400 may be repeated until the guide wire 412 has been advanced the desired amount (for example, when the percutaneous device reaches the target lesion or reaches the appropriate branch). The operation of drive assembly 400 results in reciprocating or intermittent linear movement of the guide wire 412.

For retraction of the guide wire 412, the proximal pinch 404 (and body 402) is moved to the second position proximate to the distal pinch 406. Proximal pinch is then actuated to engage (e.g. grip or pinch) the guide wire 412. The distal pinch 406 is then actuated to disengage from the guide wire 412. Linear drive mechanism 418 is then used to retract body 402, proximal pinch 404 and guide wire 412 a predetermined distance from the second position to the first position. After the guide wire 412 is retracted to the first position, the distal pinch 406 is actuated to engage (e.g., grip or pinch) to fix the guide wire 412. Proximal pinch 404 is then actuated to disengage from or release the guide wire 412. Linear drive mechanism 418 is then used to advance the body 402 and proximal pinch 404 and return to the second position. Once proximal pinch 404 is returned to the second position, the process may begin again to retract the guide wire 412 by another stroke length. Accordingly, proximal pinch 404 is actuated to engage the guide wire 412. Distal pinch 406 is then disengaged and guide wire 412 may be retracted the stroke length distance. The steps to retract the guide wire 412 with drive assembly 400 may be repeated until the guide wire 412 has been retracted the desired amount.

For rotation of the guide wire 412, proximal pinch 404 is actuated to engage the guide wire 412 and distal pinch is actuated to disengage from the guide wire 412. Rotational drive mechanism 422 is then used to rotate the body 402 and proximal pinch 404 to cause the guide wire 412 to rotate about its longitudinal axis. Preferably, proximal pinch 404 is configured to rotate with the body 402 and guide wire 412. The guide wire 412 may be rotated in any direction about its longitudinal axis. In one embodiment, rotational drive mechanism 422 may be designed to operate with a quick release mechanism so that it is responsive to user input. In one embodiment, the guide wire 412 may be rotated a predetermined amount. In another embodiment, the guide wire may be rotated in a first direction and then in a second direction. In yet another embodiment, the guide wire 412 may be rotated while it is being advanced or the guide wire 412 may be rotated while it is being retracted.

Computer-executable instructions for controlling a device drive for a catheter procedure system according to the above-described method may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which can be used to store the desired instructions and which may be accessed by system 10 (shown in FIG. 1), including by internet or other computer network form of access.

This written description used examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made to the present invention without departing from the spirit thereof. The scope of these and other changes will become apparent from the appended claims.

What is claimed is:

1. A drive assembly for a catheter procedure system comprising:
   a body configured to receive a percutaneous device;
   a proximal pinch configured to advance along the body to releasably engage the percutaneous device and to rotate with rotation of the body and the percutaneous device;
   a distal pinch configured to releasably engage the percutaneous device; and
   a linear drive mechanism coupled to the body, the linear drive mechanism configured to move the body to cause linear movement of the percutaneous device in a first direction while the proximal pinch is engaged with the percutaneous device and the distal pinch is disengaged from the percutaneous device.

2. A drive assembly according to claim 1, wherein the percutaneous device is an elongated medical device.

3. A drive assembly according to claim 1, wherein the proximal pinch is a bi-stable mechanism.

4. A drive assembly according to claim 1, wherein the distal pinch is a bi-stable mechanism.

5. A drive assembly according to claim 1, wherein the linear drive mechanism moves the body from a first position to a second position to advance the percutaneous device when the proximal pinch is engaged with the percutaneous device and the distal pinch is disengaged from the percutaneous device.

6. A drive assembly according to claim 5, wherein the linear drive mechanism moves the body from the second position to the first position to retract the percutaneous device when the proximal pinch is engaged with the percutaneous device and the distal pinch is disengaged from the percutaneous device.

7. A drive assembly according to claim 5, further comprising a rotational drive mechanism configured to rotate the proximal pinch and the body when the proximal pinch is engaged with the percutaneous device and the distal pinch is disengaged from the percutaneous device.

8. A drive assembly according to claim 1, wherein the linear drive mechanism is a linear slide.

9. A drive assembly according to claim 1, further comprising a rotational drive mechanism comprising:
   a first gear coupled to the second end of the body; and
   a second gear in mechanical contact with the first gear.

10. A drive assembly according to claim 9, further comprising a rotary motor coupled to the rotational drive mechanism.

11. A drive assembly according to claim 1, further comprising a linear motor coupled to the linear drive mechanism.

12. A catheter procedure system comprising:
   a bedside system comprising:
   at least one drive assembly, the at least one drive assembly comprising:
   a body having a first end and a second end, the second end of the body configured to receive a percutaneous device;
   a distal pinch configured to releasably engage the percutaneous device;
   a proximal pinch configured to advance along the body to the first end to releasably engage the percutaneous device and to rotate with rotation of the body and the percutaneous device;
   a linear drive mechanism coupled to the body, the linear drive mechanism configured to move the body to cause linear movement of the percutaneous device in a first direction while the proximal pinch is engaged with the percutaneous device and the distal pinch is disengaged from the percutaneous device; and
   a cassette housing enclosing the distal pinch, the proximal pinch, and the linear drive mechanism; and
   a controller coupled to the bedside system and a user interface, the controller configured to control the drive assembly to cause movement of the percutaneous device.

13. A catheter procedure system according to claim 12, wherein the bedside system further comprises a housing and the at least one drive assembly is disposed within the housing.

14. A catheter procedure system according to claim 12, wherein the percutaneous device is an elongated medical device.

15. A catheter procedure system according to claim 12, wherein the proximal pinch is a bi-stable mechanism.

16. A catheter procedure system according to claim 12, wherein the distal pinch is a bi-stable mechanism.

17. A catheter procedure system according to claim 12, wherein the linear drive mechanism moves the body from a first position to a second position to advance the percutaneous device when the proximal pinch is engaged with the percutaneous device and the distal pinch is disengaged from the percutaneous device.

18. A catheter procedure system according to claim 17, wherein the linear drive mechanism moves the body from the second position to the first position to retract the percutaneous device when the proximal pinch is engaged with the percutaneous device and the distal pinch is disengaged from the percutaneous device.

19. A catheter procedure system according to claim 17, further comprising a rotational drive mechanism configured to rotate the proximal pinch and the body when the proximal pinch is engaged with the percutaneous device and the distal pinch is disengaged from the percutaneous device.

20. A drive assembly for a catheter procedure system comprising:

a body having a first end and a second end, the second end of the body configured to receive a percutaneous device;

a proximal pinch positioned on the body, the proximal pinch configured to advance along the body to the first end to releasably engage the percutaneous device and to rotate with rotation of the body and the percutaneous device;

a rotational drive mechanism coupled to the body and comprising a first gear coupled to the second end of the body and a second gear in mechanical contact with the first gear, the rotational drive mechanism configured to rotate the body and the proximal pinch to cause the percutaneous device to rotate about a longitudinal axis of the percutaneous device;

a distal pinch configured to releasably engage the percutaneous device; and a linear drive mechanism coupled to the body, the linear drive mechanism configured to move the body and the proximal pinch while the proximal pinch is engaged with the percutaneous device and the distal pinch is disengaged from the percutaneous device to cause linear movement of the percutaneous device over a first distance along the longitudinal axis of the percutaneous device.

* * * * *